United States Patent [19]

Owen et al.

[11] 4,391,518

[45] Jul. 5, 1983

[54] DUAL LASER OPTICAL SYSTEM AND METHOD FOR STUDYING FLUID FLOW

[75] Inventors: Robert B. Owen; William K. Witherow, both of Huntsville, Ala.

[73] Assignee: The United States of America as represented by the Administrator of the National Aeronautics and Space Administration, Washington, D.C.

[21] Appl. No.: 224,232

[22] Filed: Jan. 12, 1981

[51] Int. Cl.³ .................................. G01N 21/41
[52] U.S. Cl. ........................................ 356/129
[58] Field of Search ............... 356/128, 129, 361, 32; 73/147

[56] References Cited

U.S. PATENT DOCUMENTS

| 3,623,361 | 11/1971 | Funk ........................... 356/129 |
| 3,625,619 | 12/1971 | Scholdstrom ............... 356/128 |
| 3,822,098 | 7/1974 | Rudder et al. .............. 356/407 |

FOREIGN PATENT DOCUMENTS

| 1236232 | 3/1967 | Fed. Rep. of Germany ...... 356/129 |
| 188061 | 12/1966 | U.S.S.R. ........................ 356/129 |
| 199491 | 11/1967 | U.S.S.R. ........................ 356/129 |

OTHER PUBLICATIONS

Diebold et al., "Differential Photodiode Detector for a Shock Tube Laser Schlieren System", *Rev. Sci. Instrum.*, vol. 45, No. 6, Jun. 1974, pp. 773–775.

*Primary Examiner*—R. A. Rosenberger
*Attorney, Agent, or Firm*—J. H. Beumer; J. R. Manning; L. D. Wofford, Jr.

[57] ABSTRACT

A dual laser optical system and method is disclosed for visualization of phenomena in transparent substances which induce refractive index gradients such as fluid flow and pressure and temperature gradients in fluids and gases. According to the invention two images 68 and 70 representing mutually perpendicular components of refractive index gradients may be viewed simultaneously on screen 66. Two lasers 10 and 12 having wave lengths in the visible range but separated by about 1000 angstroms are utilized to provide beams 14 and 20 which are collimated into a beam 32 containing components of the different wave lengths. The collimated beam 32 is passed through a test volume 33 of the transparent substance. The collimated beam is then separated into components of the different wave lengths and focused on to a pair of knife edges arranged mutually perpendicular to produce and project images 68 and 70 onto screen 66.

6 Claims, 1 Drawing Figure

DUAL LASER OPTICAL SYSTEM AND METHOD FOR STUDYING FLUID FLOW

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

Heretofore, an optical system commonly known as the Schlieren system has been utilized to study density gradients in transparent substances by viewing refractive index gradients. In the Schlieren method, light from a slit is collimated from a lens and focused onto a knife edge by a second lens. The text volume being studied is placed between the two lenses and the deflection pattern that results is viewed on a screen placed behind the knife edge. The deflection is related to the refractive index gradients which is, in turn, related to the density gradient in the test volume. A more complete discussion of Schlieren apparatus may be found in Liepmann and Roshko, *Elements of Gas Dynamics*, Wiley & Sons, Inc., New York, 1957. However, the conventional system is capable of visualizing only one component of the index gradient at a time.

It is advantageous to be able to observe two perpendicular components simultaneously in a dynamic situation so that both components can be correlated. Without such correlation, it is impossible to tell which physical features are causing which phenomena. For example, in a moving fluid, information would be lost when adjustment is made from one knife edge position showing one gradient component to another knife edge position showing a different gradient component. The image changes during this time period, and this would be true in any dynamic situation wherein a test volume is changing its refractice index in some way. In such a situation, it is impossible to track one particular part of the fluid flow image and to correlate it with the other image showing a different concentration gradient component. Either the density is changing, fluid motion is occurring, or some changes are being made in the specimen during the observation period; the material specimen is being stressed so that it is changing.

SUMMARY OF THE INVENTION

Accordingly, an important object of the present invention is to provide an optical system and method for visualizing perpendicular components of refractive index gradients simultaneously in studying fluid flow phenomena.

According to the present invention, the objectives are accomplished by providing a pair of lasers having a wave length in the visible length range separated by at least 1,000 angstroms, combining the beams followed by expanding the beams through a spatial filter whereupon the combined expanded beam is collimated and directed through the test volume. After passing through the test volume, the resulting beam is focused onto a transmission grating which separates the combined beam into separate beams of the different wave length components which are focused and directed to a pair of knife edges arranged mutually perpendicular to each other. The beams and any resulting deflection of the image pattern are directed by means of mirrors onto a screen which displays the images of the perpendicular components of the refractive index gradients.

Apparatus for carrying out the method of the invention preferably includes a helium-neon laser and an argon laser and two mutually perpendicular knife edges combined with conventional optical apparatus so arranged to carry out the method according to the invention.

DESCRIPTION OF THE DRAWING

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF PREFERRED EMBODIMENT

Figure 1:
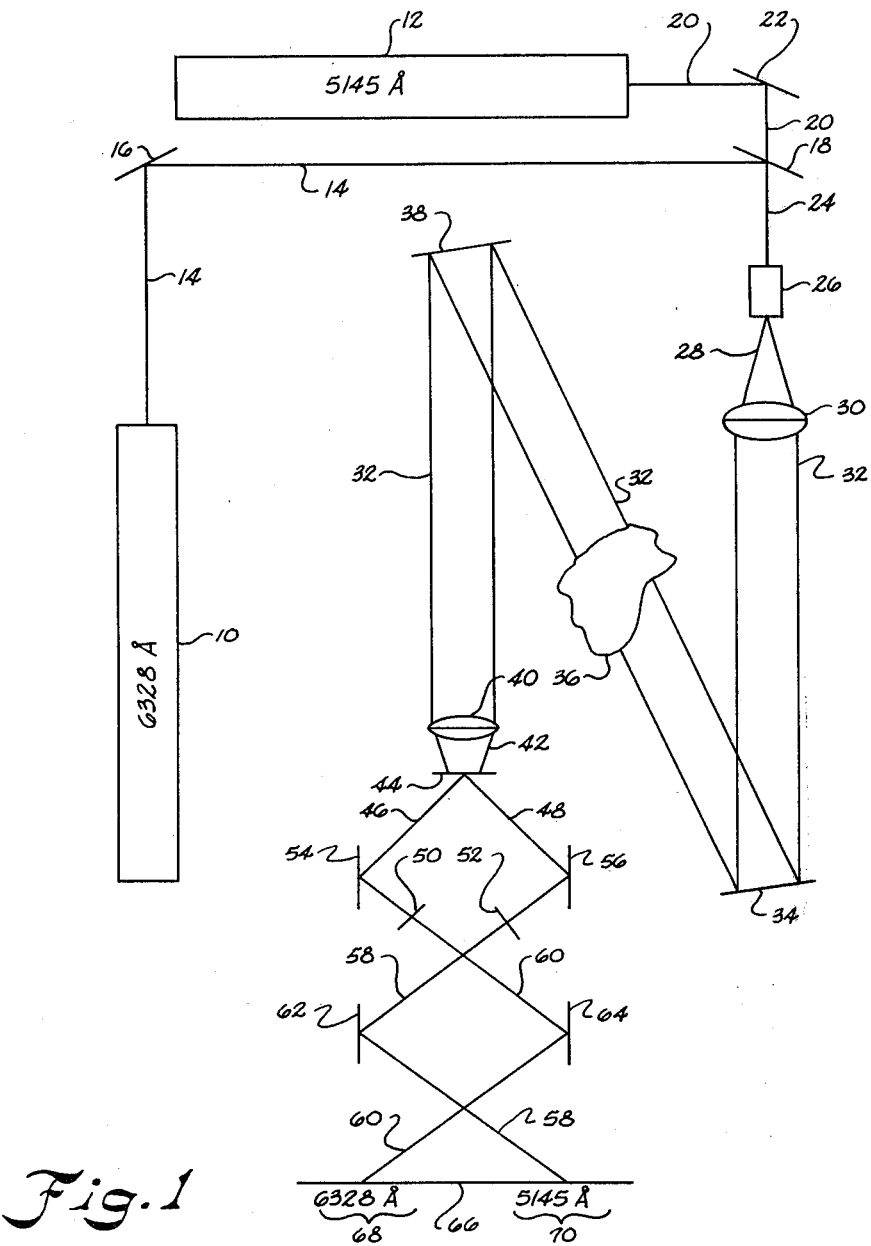
FIG. 1 is a schematic diagram illustrating an optical system and system for simultaneously visualizing perpendicular components of a refractive index-density gradient according to the invention.

Referring now to the drawing, an optical system and method for simultaneously visualizing perpendicular components of refractive index gradients is illustrated as including a pair of conventional lasers 10 and 12, wherein laser 10 is preferably a helium-neon laser having a wave length of 6328 angstroms and laser 12 is an argon laser having a wave length of 5145 angstroms. The laser beam 14 from laser 10 is directed 90° by a mirror 16 toward a beam splitter 18. The laser beam 20 from laser 12 is reflected and directed by a mirror 22 to beam splitter 18 which combines beams 14 and 20 into beam 24 which is directed to a spatial filter 26. The combined beam 24 is expanded by the spatial filter at 28 and directed to a collimating lens 30. The spatial filter 26 may include a conventional expansion lens and pinhole arrangement. The pinhole is located at the focal point of collimating lens 30 which may be any conventional double convex lens. Lens 30 collimates the beam 28 and the collimated beam 32 is directed to a mirror 34 which reflects the beam toward a test volume 36 which is the subjected of analysis.

The beam 32, passing through the test volume, is reflected by a mirror 38 to focus lens 40. The focus lens 40 focuses the beam at 42 through a conventional transmission grating 44 such as a high frequency linear grating which separates combined beam 42 into beams 46 and 48 of the above described two different wave length components. Components 46 and 48 are focused on knife edges 50 and 52 by means of suitable mirrors 54 and 56, respectively. Knife edges 50 and 52 are located at the focal point of lens 40 by adjustment in a conventional manner. The knife edges can be separately manipulated for each component beam, and by setting the knife edges mutually perpendicular, the desired mutually perpendicular refractive index gradients can be viewed simultaneously. The resulting beams 58 and 60 passed by the knife edges 52 and 50, respectively, are reflected and directed by mirrors 62 and 64 onto a screen 66 where images 68 and 70 of the mutually perpendicular components of the refractive index are viewed simultaneously.

Any suitable constant wave length lasers may be utilized at 10 and 12 as long as the difference in wave lengths between the two lasers is at least 1000 angstroms and stays in the visible wave length range. This enables grating 44 to separate the beams adequately to allow spatial arrangement of mirrors 54, 56, 62, 64, and efficient transmission of the images on screen. Reflective mirrors of any suitable type may be utilized such as flat surface aluminum mirrors. The lenses are illustrated as conventional double convex lens.

Beam splitter 18 may be any suitable beam splitter such as a conventional refractive cube or prism. While it is possible for the beam to be split by a reflective beam splitter, such a system would lead to increased optical abberations due to beam path asymmetrics.

While a preferred embodiment of the invention has been described using specific terms, such description is for illustrative purposes only, and it is to be understood that changes and variations may be made without departing from the spirit or scope of the following claims.

What is claimed is:

1. A method of producing and visualizing simultaneous images of perpendicular components of refractive index gradients in transparent substances comprising the steps of:
   providing two laser beams, each said beam having a different wave length;
   combining and collimating said two laser beams into a single beam containing said two different wave length components;
   providing a test volume which includes said transparent substance;
   passing said collimated beam through said test volume;
   separating said collimated beam into two separate beams having said different wave lengths;
   providing two separate knife edges arranged mutually perpendicular to one another;
   focusing a first of said separated beams on one of said knife edges and a second of said beams on the other of said knife edges;
   projecting light allowed to be passed by said knife edges onto a viewing means; and
   producing visual images of mutually perpendicular refractive index gradients passed by said knife edges on said viewing means for simultaneous viewing.

2. The method of claim 1 wherein said wave lengths are in the visible wave length range.

3. The method of claim 2 wherein the difference in wave length between said two beams is equal to or greater than about one-thousand angstroms.

4. The method of claim 1 including expanding said single combined beam prior to collimating said beam.

5. A dual laser optical system for producing and visualizing simultaneous images of perpendicular components of refractive index gradients in transparent substances comprising:
   a first laser beam having a predetermined wave length;
   a second laser beam having predetermined wave length;
   said wave lengths of said first and second laser beams being in the visible wave length range and being of different wave lengths from one another;
   means for combining and collimating said two laser beams into a single beam containing components of said two different wave lengths;
   first mirror means for reflecting and directing said collimated beam through a test volume of the substance being studied;
   a pair of knife edges arranged mutually perpendicular with one another;
   grating means for separating the individual components of said collimated beam into a first separated beam and a second beam, respectively, of said different wave lengths;
   second mirror means for focusing said separated beams onto said knife edges; and
   means for viewing images of the deflection patterns of said beams passed by said knife edges;
   third mirror means for projecting said beams onto said viewing means after passing said knife edge; and
   said viewing means producing images of a pair of mutually perpendicular components of refractive index gradients for simultaneous viewing of said images.

6. The system of claim 5 wherein said first and second laser beams have wave lengths in the visible range, and said respective wave lengths are separated by approximately 1000 angstroms.

* * * * *